US011896595B2

(12) United States Patent
Schaub et al.

(10) Patent No.: US 11,896,595 B2
(45) Date of Patent: *Feb. 13, 2024

(54) JAK1 PATHWAY INHIBITORS FOR THE TREATMENT OF CHRONIC LUNG ALLOGRAFT DYSFUNCTION

(71) Applicant: Incyte Corporation, Wilmington, DE (US)

(72) Inventors: Richard L. Schaub, West Chester, PA (US); Kevin O'Hayer, Bryn Mawr, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/854,443

(22) Filed: Jun. 30, 2022

(65) Prior Publication Data

US 2022/0331325 A1   Oct. 20, 2022

Related U.S. Application Data

(63) Continuation of application No. 16/810,045, filed on Mar. 5, 2020, now Pat. No. 11,406,640.

(60) Provisional application No. 62/814,085, filed on Mar. 5, 2019.

(51) Int. Cl.
*A61K 31/519* (2006.01)
*A61P 37/06* (2006.01)

(52) U.S. Cl.
CPC ............ *A61K 31/519* (2013.01); *A61P 37/06* (2018.01)

(58) Field of Classification Search
CPC .................................................. A61K 31/519
See application file for complete search history.

(56) References Cited

U.S. PATENT DOCUMENTS

| | | | |
|---|---|---|---|
| 7,598,257 B2 | 10/2009 | Rodgers et al. | |
| 8,410,167 B2 | 4/2013 | Radzik et al. | |
| 8,691,807 B2 | 4/2014 | Yao et al. | |
| 8,716,303 B2 | 5/2014 | Rodgers et al. | |
| 8,722,693 B2 | 5/2014 | Rodgers et al. | |
| 8,765,734 B2 | 7/2014 | Huang et al. | |
| 8,933,085 B2 | 1/2015 | Rodgers et al. | |
| 8,987,443 B2 | 3/2015 | Lin et al. | |
| 9,034,884 B2 | 5/2015 | Rodgers et al. | |
| 9,181,271 B2 | 11/2015 | Li et al. | |
| 9,193,733 B2 | 11/2015 | Rodgers et al. | |
| 9,249,145 B2 | 2/2016 | Rodgers et al. | |
| 9,249,149 B2 | 2/2016 | Silverman et al. | |
| 9,359,358 B2 | 6/2016 | Rodgers et al. | |
| 9,382,231 B2 | 7/2016 | Li et al. | |
| 9,487,521 B2 | 11/2016 | Zhou et al. | |
| 9,498,467 B2 | 11/2016 | Leopold et al. | |
| 9,540,367 B2 | 1/2017 | Tung | |
| 9,655,854 B2 | 5/2017 | Yeleswaram et al. | |
| 9,802,957 B2 | 10/2017 | Zhou et al. | |
| 11,406,640 B2 * | 8/2022 | Schaub ............... | A61K 31/519 |
| 2007/0219223 A1 | 9/2007 | Wilson et al. | |
| 2009/0075875 A1 | 3/2009 | Hoffman et al. | |
| 2010/0298334 A1 | 11/2010 | Rodgers et al. | |
| 2011/0059951 A1 | 3/2011 | Rodgers et al. | |
| 2011/0224190 A1 | 9/2011 | Huang et al. | |
| 2012/0122846 A1 | 5/2012 | Calderwood et al. | |
| 2012/0149681 A1 | 6/2012 | Rodgers et al. | |
| 2012/0149682 A1 | 6/2012 | Rodgers et al. | |
| 2013/0018034 A1 | 1/2013 | Yao et al. | |
| 2013/0045963 A1 | 2/2013 | Rodgers et al. | |
| 2013/0060026 A1 | 3/2013 | Zhou et al. | |
| 2014/0005166 A1 | 1/2014 | Rodgers et al. | |
| 2014/0121198 A1 | 5/2014 | Li et al. | |
| 2014/0256941 A1 | 9/2014 | Liu et al. | |
| 2014/0343030 A1 | 11/2014 | Li et al. | |
| 2015/0065484 A1 | 3/2015 | Yeleswaram et al. | |
| 2015/0118229 A1 | 4/2015 | Voss et al. | |
| 2015/0246046 A1 | 9/2015 | Vaddi | |
| 2015/0344497 A1 | 12/2015 | Zhou et al. | |
| 2017/0121327 A1 | 5/2017 | Fatheree et al. | |
| 2018/0258087 A1 | 9/2018 | Fatheree et al. | |
| 2018/0258088 A1 | 9/2018 | Fatheree et al. | |
| 2018/0311226 A1 | 11/2018 | Thalladi et al. | |
| 2018/0311255 A1 | 11/2018 | Fatheree et al. | |
| 2019/0233392 A1 | 8/2019 | Wang et al. | |
| 2019/0255053 A1 | 8/2019 | Montgomery et al. | |
| 2019/0328739 A1 | 10/2019 | Howell et al. | |
| 2019/0331697 A1 | 10/2019 | Howell et al. | |
| 2020/0129517 A1 | 4/2020 | Assad | |
| 2020/0197399 A1 | 6/2020 | Yeleswaram et al. | |
| 2020/0281931 A1 | 9/2020 | Shaub et al. | |

(Continued)

FOREIGN PATENT DOCUMENTS

| | | |
|---|---|---|
| CN | 108366994 | 8/2018 |
| WO | WO 2002/000196 | 1/2002 |
| WO | WO 2011/068881 | 6/2011 |

(Continued)

OTHER PUBLICATIONS

Atzrodt et al., "The Renaissance of H/D Exchange," Angew Chem Int Ed., 2007, 46:7744-7765.
Benden et al., "Extracorporeal photopheresis after lung transplantation: a 10-year single-center experience," Transplantation, 2008, 86:1625-1627.
Berge et al., "Pharmaceutical Salts," J Pharm Sci., 1977, 66(1):1-19.
Boehler et al., "Post-transplant bronchiolitis obliterans," Eur Respir J., 2003, 22:1007-1018.
Chambers et al. "The International Thoracic Organ Transplant Registry of the International Society for Heart and Lung Transplantation: Thirty-fifth adult lung and heart-lung transplant report—2018; Focus theme: multiorgan transplantation," J Heart Lung Transplant., 2018, 37:1169-1183.
Chambers et al., "The Registry of the International Society for Heart and Lung Transplantation: Thirty-fourth Adult Lung And Heart-Lung Transplantation Report—2017; Focus Theme: Allograft ischemic time," JHLT, 2017, 36(10):1047-1059.

(Continued)

*Primary Examiner* — Paul V Ward
(74) *Attorney, Agent, or Firm* — Fish & Richardson P.C.

(57) ABSTRACT

This disclosure relates to JAK1 pathway inhibitors and the use thereof in treating chronic lung allograft dysfunction such as, e.g., bronchiolitis obliterans syndrome.

17 Claims, No Drawings

(56) References Cited

U.S. PATENT DOCUMENTS

2020/0348313 A1  11/2020  Howell et al.

FOREIGN PATENT DOCUMENTS

| WO | WO 2015/021153 | 2/2015 |
|---|---|---|
| WO | WO 2015/131031 | 9/2015 |
| WO | WO 2018/099680 | 6/2018 |

OTHER PUBLICATIONS

Cooke et al, "The biology of chronic graft-versus-host disease: a task force report from the National Institutes of Health Consensus Development Project on Criteria for Clinical Trials in Chronic Graft-versus-Host Disease," Biol Blood Marrow Transplant., 2017, 23:211-234.

Estenne et al., "Bronchiolitis obliterans syndrome 2001: an update of the diagnostic criteria," J Heart Lung Transplant., Mar. 2002, 21(3):297-310.

Eurasian Office Action in Eurasian Application No. 202192426, dated Oct. 17, 2022, 6 pages.

FDA.gov, "Drug Development and Drug Interactions: Table of Substrates, Inhibitors and Inducers," Food and Drug Administration, last updated Mar. 10, 2020[retrieved on Sep. 8, 2020], retrieved from URL <https://www.fda.gov/drugs/drug-interactions-labeling/drug-development-and-drug-interactions-table-substrates-inhibitors-and-inducers>, 18 pages.

Fukami et al., "An obligatory role for lung infiltrating B cells in the immunopathogenesis of obliterative airway disease induced by antibodies to MHC class I molecules," Am J Transplant, 2012, 12:867-876.

Gennaro, "Performulation," Remington's Pharmaceutical Sciences, 17th Ed., Mack Publishing Company, Easton, PA, 1985, p. 1418.

Gorospe Sarasua et al., "Radiological Improvement of Bronchiolitis Obliterans Following Hematopoietic Stem Cell Transplantation in a Patient Treated with Ruxolitinib," Archivos De Bronconeumologia, Dec. 1, 2018, 54(12):640-642.

Gupta et al., "IL-17A blockade attenuates obliterative bronchiolitis and IFN-γ cellular immune response in lung allografts," Am J Respir Cell Mol Biol., 2017, 56:708-715.

Hodge et al, "Bronchiolitis obliterans syndrome is associated with increased peripheral blood natural killer and natural killer T-like granzymes, perforin, and T-helper-type 1 pro-inflammatory cytokines," J Heart Lung Transplant., 2012, 31:888-895.

International Preliminary Report on Patentability in International Application No. PCT/US2020/021088, dated Aug. 25, 2021, 7 pages.

International Search Report and Written Opinion in International Application No. PCT/US2020/021088, dated Jun. 8, 2020, 14 pages.

Jagasia et al., "Ruxolitinib for the treatment of patients with steroid-refractory GVHD: an introduction to the REACH trials," Immunotherapy 2018, 10:391-402.

Kerekes et al., "Aurora Kinase Inhibitors Based on the Imidazo[1,2-a]pyrazine Core: Fluorine and Deuterium Incorporation Improve Oral Absorption and Exposure." J Med Chem., 2011, 54(1):201-210.

Khoury et al., "Ruxolitinib a steroid sparing agent for chronic graft versus host disease," Bone Marrow Transplant, 2018, 53(7):826-831.

Leonard et al., "Dendritic cells and macrophages in lung allografts: A role in chronic rejection?" Am J Respir Crit Care Med., 2000, 161:1349-1354.

Meyer et al., "An international ISHLT/ATS/ERS clinical practice guideline: diagnosis and management of bronchiolitis obliterans syndrome," Eur Respir J., 2014, 44:1479-1503.

Miller et al., "Standardisation of spirometry," Eur Respir J., 2005, 26:319-338.

Park et al., "Homogeneous proximity tyrosine kinase assays: scintillation proximity assay versus homogeneous time-resolved fluorescence," Analytical Biochemistry, 1999, 269:94-104.

Philit et al., "Post-transplant obstructive lung disease ("bronchiolitis obliterans"): a clinical comparative study of bone marrow and lung transplant patients," Eur Respir J., 1995, 8:551-558.

Ruttens et al., "Montelukast for bronchiolitis obliterans syndrome after lung transplantation: A randomized controlled trial," PLOS One, Apr. 6, 2018, 13:e0193564.

Sarahrudhi et al., "International experience with conversion from cyclosporine to tacrolimus for acute and chronic lung allograft rejection," JTCS, Apr. 2004, 127(4):1126-1132.

Sato et al., "Restrictive allograft syndrome (RAS): a novel form of chronic lung allograft dysfunction," J Heart Lung Transplant, 2011, 30:735-742.

Schoettler et al., "Ruxolitinib and Steroid Refractory/Dependent Bronchiolitis Obliterans after Hematopoietic Cell Transplantation: A Steroid Sparing Agent that also Resulted in Improved Lung Function in Children," 60th Annual Meeting of the American-Society-of-Hematology, San Diego, CA, Dec. 1-4, 2018, Nov. 29, 2018, 132(Suppl. 1):3407.

Schoettler et al., "Ruxolitinib is an effective steroid sparing agent in children with steroid refractory/dependent bronchiolitis obliterans syndrome after allogenic hematopoietic cell transplantation," Bone Marrow Transplantation, Jan. 25, 2019, 54(7):1158-1160.

Schroeder et al., "A Phase I study of Janus kinase inhibition with INCB039110 in acute GVHD," Blood, 2016, Presented at the 58th American Society of Hematology (ASH) Annual Meeting & Exposition, Dec. 3-6, 2016, San Diego, CA, 128(22):390.

Spoerl et al., "Response to JAK1/2 inhibition in patients with corticosteroid- refractory acute graft-versus-host disease," Blood, 2014, 124(21):3934.

Thomas et al., "Survival after lung retransplantation in the United States in the current era (2004 to 2013): better or worse?" Ann Thorac Surg., 2015, 100:452-457.

Vos et al. "Long-term azithromycin therapy for bronchiolitis obliterans syndrome: divide and conquer?," JHLT, 2010, 29(12):1358-1368.

Vos et al., "A randomised controlled trial of azithromycin to prevent chronic rejection after lung transplantation," Eur Respir J., 2011, 37:164-172.

Xu et. al., "Design, synthesis and biological evaluation of deuterated nintedanib for improving pharmacokinetic properties," J Label Compd Radiopharm., 2015, 58:308-312.

Zeiser et al., "Ruxolitinib in corticosteroid-refractory graft-versus-host-disease after allogeneic-stem cell transplantation: a multi-center survey," 2015, Leukemia, 29(10):2062-2068.

Office Action in Chinese Appln. No. 202080024215.0, dated Sep. 26, 2023, 41 pages (with English Translation).

Office Action in European Appln. No. 20713496.6, dated Nov. 15, 2023, 4 pages.

* cited by examiner

JAK1 PATHWAY INHIBITORS FOR THE TREATMENT OF CHRONIC LUNG ALLOGRAFT DYSFUNCTION

TECHNICAL FIELD

This disclosure relates to JAK1 pathway inhibitors and the use thereof in treating chronic lung allograft dysfunction, e.g., bronchiolitis obliterans syndrome.

BACKGROUND

Allogeneic lung transplantation is an effective therapy for the treatment of a variety of end-stage lung disorders, including COPD, ILD, cystic fibrosis and others. More than 4000 lung transplants were performed worldwide in 2016, with approximately 2300 of these having been performed in the United States. (2018 OPTN/SRTR Registry). Although 1 and 3 year survival rates post-transplant have improved, long term survival rates from transplant have remained stagnant with a median overall survival of 6.1 years (Chambers, D. et al. *JHLT*, 2017, Vol. 36, No. 10). The most common cause of death from lung transplant after 1 year from surgery is chronic lung allograft dysfunction (CLAD); the most common subset of CLAD is bronchiolitis obliterans syndrome (BOS). Post-lung transplant BOS affects approximately 50% of patients who survive past 5 years and is the leading cause of death for those who survive past 1 year post-transplant (Chambers, D. et al. *JHLT*, 2017, Vol. 36, No. 10). Post-lung transplant BOS is characterized by an allo-reactive immune infiltrate which ultimately leads to progressive bronchiolar ectasia, fibrosis and ultimately organ failure (Boehler, A. et al. *Eur Respir J. Vol* 22., No. 6 1007-1018, 2003). Despite prophylactic treatments with immunosuppressive agents, the rate of post-lung transplant BOS remains unchanged. There are few therapeutic trials for post-lung transplant BOS, and currently no agents are approved by the FDA for either the prevention or treatment of post-lung transplant BOS. Interventions that have been investigated in the treatment of post-lung transplant BOS including azithromycin, altering immunosuppressive regimens, everolimus, montelukast, aerosolized cyclosporine, aerosolized tacrolimus, alemtuzumab, total lymphoid irradiation, photopheresis, and ultimately re-transplantation. Of these, the only definitive therapy for progressive BOS for those who are eligible is lung re-transplantation. Survival following a second transplant is markedly lower than primary transplants at 2.6 years (Thomas, M. et al., *Ann. Thorac. Surg.* 2015; 100:452-7).

Accordingly, there is a need to develop new therapies for the prevention and treatment of chronic lung allograft dysfunction, e.g., bronchiolitis obliterans syndrome. This application addresses this need and others.

SUMMARY

Provided herein are methods for the treatment of chronic lung allograft dysfunction (e.g., bronchiolitis obliterans syndrome) in a subject in need thereof, comprising administering to said subject a therapeutically effective amount of a JAK1 pathway inhibitor, or a pharmaceutically acceptable salt thereof.

Provided herein is a JAK1 pathway inhibitor for the treatment of chronic lung allograft dysfunction (e.g., bronchiolitis obliterans syndrome) in a subject in need thereof.

Provided herein is a use of a JAK1 pathway inhibitor for manufacture of a medicament for use in treating chronic lung allograft dysfunction (e.g., bronchiolitis obliterans syndrome) in a subject in need thereof.

DETAILED DESCRIPTION

The present invention provides, inter alia, a method for treating chronic lung allograft dysfunction, e.g., bronchiolitis obliterans syndrome, in a subject in need thereof, comprising administering to said subject a therapeutically effective amount of a JAK1 pathway inhibitor, e.g., JAK1/2 inhibitor or JAK1 inhibitor, or a pharmaceutically acceptable salt thereof.

The diagnosis of post-lung transplant BOS can be made clinically and can be defined by a persistent decline in lung function as measured by $FEV_1$. To make the diagnosis of post-lung transplant BOS, other causes of post-transplant decline including acute rejection, infection, native lung problems for single lung recipients, excessive recipient weight gain, anastomotic dysfunction, respiratory muscle dysfunction, effusion, or technical problems such as erroneous measurements due to device dysfunction as well as others can be excluded as the cause of lung graft dysfunction. (Meyer, K. C., et al. *Eur. Respir.* 1 2014; 44: 1479-1503).

The BOS classification scheme, the accepted grading system for post-lung transplant BOS, can be based off of spirometric evaluation of a persistent decline in $FEV_1$ to ≤80% of baseline post-transplant baseline $FEV_1$. Baseline can be defined as the average of the two best $FEV_1$ (or $FEF_{25-75\%}$) values ≥3 weeks apart following functional recovery and stabilization post-lung transplantation. The most recent update provided below includes a new classification, Grade 0p, which was added to ensure early diagnosis of post-lung transplant BOS. (Meyer, K. C., et al. *Eur. Respir.* 1 2014; 44: 1479-1503). Table 1 was adapted from Meyer, K. C., et al. *Eur. Respir. J.* 2014; 44: 1479-1503, which is hereby incorporated by reference in its entirety. $FEV_1$: Forced Expiratory Volume in 1 second; $FEF_{25-75\%}$: Forced Expiratory Flow at 25-75% of forced vital capacity.

TABLE 1

BOS Classification Scheme

| BOS Grade | Definition |
| --- | --- |
| 0 | $FEV_1 > 90\%$ and $FEF_{25-75\%} > 75\%$ |
| 0p | $FEV_1$ 81-90% and $FEF_{25-75\%} \leq 75\%$ |
| 1 | $FEV_1$ 66-80% |
| 2 | $FEV_1$ 51-65% |
| 3 | $FEV_1 \leq 50\%$ |

There is no standard of care or consensus treatment algorithm tor BOS therapy, and there are few high quality randomized trials which demonstrate clear benefit in BOS patients (Meyer, K. C., et al. *Eur. Respir.* 1 2014; 44: 1479-1503).

The methods described herein utilize JAK1 pathway inhibitors, particularly JAK1/2 and JAK1 selective inhibitors. JAK1 plays a central role in a number of cytokine and growth factor signaling pathways that, when dysregulated, can result in or contribute to disease states. JAK1 has been shown to cooperate with other JAKs to mediate the signaling of a number of inflammatory cytokines associated with many inflammatory disorders.

Itacitinib, a selective JAK1 pathway inhibitor, is currently under clinical investigation in the treatment of both acute and chronic post HSCT GVHD. Chronic GVHD can affect any organ in the body with the most common being skin, liver, and intestines. Chronic GVHD can also affect the lungs and has a clinical presentation that is nearly identical to post-lung transplant BOS. The correlation between lung cGVHD and post-lung transplant BOS was first described in 1995, where clinical data and tissue were collected from 9 patients with lung cGVHD and post-lung transplant BOS. Both groups had similar signs and symptoms including progressive dyspnea and an irreversible obstructive pattern as well as similar outcomes and histology including diffuse inflammation leading to ectasia of the large bronchi (Philit et al., *Eur. Respir. J.* 1995, 8:551-558).

Lung cGVHD is initiated during the transplant process through the development of normal tissue damage that leads to a tissue damage response characterized by a release of cytokines, toll-like receptor agonists, neutrophils, platelets, and vascular inflammation (Cooke et al, *Biol. Blood Marrow Transplant* 2017, 23:211-234). CD4 and CD8 cells as well at Th17 cells are recruited to the site, however, due to thymic injury or dysfunction, there is impaired negative selection of these cells and autoreactive T-cell clones persist. In addition, the requisite immunosuppression regimens used in cGVHD including CNIs lead to $T_{reg}$ depletion. Ultimately, the initial T-cell response leads to the activation of a variety of innate and adaptive immune cells including T, B, and NK cells as well as APCs to the site, leading to upregulation of proinflammatory cytokines TGFβ, PDGFα, TNFα, and IL17. This chronic inflammation and fibroblast recruitment ends with target organ collagen deposition and with continued dysfunction, fibrosis (Cooke et al, *Biol. Blood Marrow Transplant* 2017, 23:211-234).

Many of the same biologic principles are inherent in post-lung transplant BOS. The main difference being that in cGVHD the immune response is aberrant and leads to transplanted stem cells attacking host tissue whereas in post lung transplant BOS, the immune response is physiologically normal, although it still leads to poor outcomes for patients. In post-lung transplant BOS, the inciting event for alloreactive acute inflammation phase is clear, namely, an allogeneic lung graft implant; however, it should be noted that similar to cGVHD, patients with events leading to graft tissue injury including an acute rejection episode following transplant, CMV infection as well as other tissue damaging phenomena such as GERD and cold ischemic time are more likely to develop post—lung transplant BOS (Meyer, K. C., et al. *Eur. Respir. J.* 2014; 44: 1479-1503). Thymic dysfunction seen with cGVHD is not relevant in post-lung transplant BOS as alloreactive T cells would not be negatively selected. Importantly, however, roles for an early CD4, CD8, and Th17 cell infiltrate, as well as subsequent recruitment of B cell, NK cell, and APCs are all well documented in post-lung transplant BOS, even if these are physiologically appropriate (Boehler and Estenne, *Eur. Respir.* 1 2003, 22:1007-1018; Gupta et al., *Am. J. Respir. Cell Mol. Biol.* 2017, 56:708-715; Fukami et al., *Am. J. Transplant*, 2012, 12:867-876; Hodge et al, *J. Heart Lung Transplant*, 2012, 31:888-895, Leonard et al., *Am. J. Respir. Crit. Care Med* 2000, 161:1349-1354). Similar to cGVHD, maintenance immunosuppression regimens use CNIs leading to $T_{reg}$ depletion and inhibition (Meyer, K. C., et al. *Eur. Respir.* 1 2014; 44: 1479-1503). Finally, each of the known cytokines, including TGFβ, PDGFα, TNFα, and IL-17 as well as cellular mediators of aberrant tissue repair have a documented presence in post-lung transplant BOS.

Additionally, murine models have demonstrated that prophylactic and therapeutic dosing with itacitinib led to improvement in the GVHD score at either 60 mg/kg per day or 120 mg/kg per day indicating the clinical efficacy in an alloreactive mouse model. The JAK inhibitors ruxolitinib (a JAK1/2 inhibitor) and itacitinib have demonstrated clinical efficacy in acute GVHD (aGVHD); additionally ruxolitinib has produced clinical efficacy in chronic GVHD (cGVHD).

Of note, 4 out of 5 patients in a study with lung cGVHD had $FEV_1$ responses as defined by an increase in $FEV_1$ of ≥10%. In addition, a study that examined the use of ruxolitinib in 5 pediatric patients (4 evaluable) with lung cGVHD demonstrated 2 responses with 1 patient having an increase in $FEV_1$ of 9%. Four out of five patients were able to wean steroids completely and the final patient was able to decrease the steroid requirement by >50% (Schoettler et al, *Bone Marrow Transplantation*, 2019, 54:1158-1160. In addition to ruxolitinib, itacitinib has demonstrated significant clinical activity in patients with aGVHD. A recent study evaluated the safety and efficacy of 2 doses of itacitinib, 200 mg QD and 300 mg QD, in patients with treatment naive or steroid refractory aGVHD.

Accordingly, provided herein are methods for treating chronic lung allograft dysfunction in a subject, said method comprising administering to the subject a JAK1 pathway inhibitor (e.g., a JAK1/2 inhibitor or a selective JAK1 inhibitor), or a pharmaceutically acceptable salt thereof.

In some embodiments, the chronic lung allograft dysfunction is bronchiolitis obliterans syndrome.

In some embodiments, the subject is a lung transplant recipient (e.g., a single lung transplant recipient or a double lung transplant recipient).

In some embodiments, the subject is a double lung transplant recipient.

In some embodiments, the subject suffers from Grade 0, Grade 0p, Grade 1, Grade 2, or Grade 3 bronchiolitis obliterans syndrome as determined by International Society for Heart and Lung Transplantation (ISHLT) criteria.

In some embodiments, the subject suffers from Grade 0p, Grade 1, Grade 2 or Grade 3 bronchiolitis obliterans syndrome as determined by International Society for Heart and Lung Transplantation (ISHLT) criteria.

In some embodiments, the subject suffers from Grade 1 or Grade 2 bronchiolitis obliterans syndrome as determined by International Society for Heart and Lung Transplantation (ISHLT) criteria.

In some embodiments, the subject has a fractional decrease in $FEV_1$ to less than or about 50%, 55%, 60%, 65%, 70%, 75%, 80%, 85%, 90%, or 95% of post-transplant baseline $FEV_1$. These values can be used to define a range, such as from about 50% to about 75%.

In some embodiments, the subject has a $FEF_{25-75\%}$ value of more than, less than or about 50%, 55%, 60%, 65%, 70%, 75%, 80%, 85%, 90%, or 95%. These values can be used to define a range, such as from about 60% to about 80%.

In some embodiments, the subject suffers from Grade 0 bronchiolitis obliterans syndrome, wherein Grade 0 bronchiolitis obliterans syndrome is defined as a fractional decrease in $FEV_1$ to less than 100%, but greater than 90% of post-transplant baseline $FEV_1$ and/or baseline $FEF_{25-75\%}$ of greater than 75% of post-transplant baseline.

In some embodiments, the subject suffers from Grade 0p bronchiolitis obliterans syndrome, wherein Grade 0p bronchiolitis obliterans syndrome is defined as a fractional decrease in $FEV_1$ to 81-90% of post-transplant baseline $FEV_1$ and/or baseline $FEF_{25-75\%}$ of less than or equal to 75% of post-transplant baseline.

In some embodiments, the subject suffers from Grade 1 bronchiolitis obliterans syndrome, wherein Grade 1 bronchiolitis obliterans syndrome is defined as a fractional decrease in $FEV_1$ to 66-80% of post-transplant baseline $FEV_1$.

In some embodiments, the subject suffers from Grade 2 bronchiolitis obliterans syndrome, wherein Grade 2 bronchiolitis obliterans syndrome is defined as a fractional decrease in $FEV_1$ to 51-65% of post-transplant baseline $FEV_1$.

In some embodiments, the subject suffers from Grade 3 bronchiolitis obliterans syndrome, wherein Grade 3 bronchiolitis obliterans syndrome is defined as a fractional decrease in $FEV_1$ to less than or equal to 50% of post-transplant baseline $FEV_1$.

In some embodiments, treating bronchiolitis obliterans syndrome comprises about, or greater than about, a 5%, 10%, 15%, 20%, 25%, 30%, 35%, 40%, 45% or 50% increase in $FEV_1$ at about 4 weeks, 8 weeks, 12 weeks, 3 months, 4 months, 5 months or 6 month following the first administration of the JAK1 pathway inhibitor, or a pharmaceutically acceptable salt thereof.

In some embodiments, treating bronchiolitis obliterans syndrome comprises about, or greater than about, a 5%, 10%, 15%, 20%, 25%, 30%, 35%, 40%, 45% or 50% increase in $FEV_1$ at about 4 weeks, 8 weeks, 12 weeks, 3 months, 4 months, 5 months or 6 month following the first administration of the JAK1 pathway inhibitor, or a pharmaceutically acceptable salt thereof.

In some embodiments, treating bronchiolitis obliterans syndrome comprises about, or greater than about, a 10% increase in $FEV_1$ at about 12 weeks following the first administration of the JAK1 pathway inhibitor, or a pharmaceutically acceptable salt thereof.

In some embodiments, treating bronchiolitis obliterans syndrome comprises about a 10% or greater increase in $FEV_1$ at twelve weeks following the first administration of the JAK1 pathway inhibitor, or a pharmaceutically acceptable salt thereof.

Also provided herein is a method of reducing the risk of bronchiolitis obliterans syndrome in a subject, said method comprising administering to the subject a JAK1 pathway inhibitor, or a pharmaceutically acceptable salt thereof.

Also provided herein is a method of reducing the risk of lung re-transplantation in a subject, said method comprising administering to the subject a JAK1 pathway inhibitor, or a pharmaceutically acceptable salt thereof.

Also provided herein is a method of improving the $FEV_1$ in a subject with bronchiolitis obliterans syndrome, the method comprising administering to the subject an effective amount of a JAK1 pathway inhibitor, or a pharmaceutically acceptable salt thereof.

Also provided herein is a method of improving the quality of life in a subject with bronchiolitis obliterans syndrome, the method comprising administering to the subject an effective amount of a JAK1 pathway inhibitor, or a pharmaceutically acceptable salt thereof.

Also provided herein is a method of reducing death, reducing progressive bronchiolar ectasia, reducing organ failure, reducing decline in lung function, increasing recovery and stabilization post-lung transplantation, decreasing hospitalization, decreasing health care utilization, and/or reducing the risk of re-transplantation, as well as other potential benefits as provided herein, in a subject, the method comprising administering to the subject an effective amount of a JAK1 pathway inhibitor, or a pharmaceutically acceptable salt thereof.

In some embodiments, the subject has one or more of the Inclusion Criteria listed in Example 1, infra. In some embodiments, the subject has one, two, three, four, five, or six of the inclusion criteria listed in Example 1, infra. In some embodiments, the subject has all of the inclusion criteria listed in Example 1, infra.

In some embodiments, the subject has four, three, two, one, or none of the exclusion criteria listed in Example 1, infra. In some embodiments, the subject has none of the exclusion criteria listed in Example 1, infra.

In some embodiments, the subject has all of the inclusion criteria and has none of the exclusion criteria, as listed in Example 1, infra.

Also provided herein is a method of reducing the risk of hospitalization in a subject, said method comprising administering to said subject an effective amount of a JAK1 pathway inhibitor, or a pharmaceutically acceptable salt thereof, wherein said subject is (a) diagnosed with bronchiolitis obliterans syndrome; (b) has had a lung transplantation within 1 to 5 years prior to administering the JAK1 pathway inhibitor, or a pharmaceutically acceptable salt thereof, and (c) does not have a decrease in $FEV_1$ attributable to a cause other than bronchiolitis obliterans syndrome.

The present disclosure, in some embodiments, can be directed to a method for treating non-transplant related bronchiolitis obliterans syndrome, in a subject in need thereof, comprising administering to said subject a therapeutically effective amount of a JAK1 pathway inhibitor, or a pharmaceutically acceptable salt thereof, e.g., JAK1/2 inhibitor or a pharmaceutically acceptables salt thereof, or a JAK1 inhibitor, or a pharmaceutically acceptable salt thereof.

The methods described herein utilize JAK1 pathway inhibitors, i.e., JAK1/2 inhibitors or JAK1 selective inhibitors (any of which can be in the form of a pharmaceutically acceptable salt).

I. JAK1/2 inhibitors:

In some embodiments, the JAK1/2 inhibitor is baricitinib, or a pharmaceutically acceptable salt thereof.

In some embodiments, the JAK1/2 inhibitor is ruxolitinib, or a pharmaceutically acceptable salt thereof (see e.g., U.S. Pat. No. 7,598,257, the disclosure of which is incorporated herein by reference in its entirety). In some embodiments, the salt is ruxolitinib phosphate (see e.g., U.S. Pat. No. 8,722,693, the disclosure of which is incorporated herein by reference in its entirety).

In some embodiments, the JAK1/2 inhibitor is ruxolitinib, or a pharmaceutically acceptable salt thereof, wherein one or more hydrogen atoms are replaced by deuterium atoms. In some embodiments, the JAK1/2 inhibitor is any of the compounds in US Patent 9249149 (which is incorporated herein by reference in its entirety), or a pharmaceutically acceptable salt thereof. In some embodiments, the JAK1/2 inhibitor is CTP-543 (Compound 111), or a pharmaceutically acceptable salt thereof.

In some embodiments, the JAK1/2 inhibitor is a compound of Formula I:

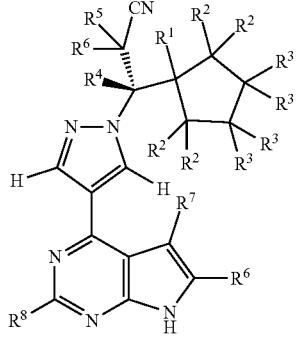

or a pharmaceutically acceptable salt thereof, wherein:
$R^1$ is selected from H and D;
each $R^2$ is independently selected from H and D, provided that each $R^2$ attached to a common carbon is the same;
each $R^3$ is independently selected from H and D, provided that each $R^3$ attached to a common carbon is the same;
$R^4$ is selected from H and D;
each $R^5$ is the same and is selected from H and D; and
$R^6$, $R^7$, and $R^8$ are each independently selected from H and D; provided that when $R^1$ is H, each $R^2$ and each $R^3$ are H, $R^4$ is H, and each of $R^6$, $R^7$, and $R^8$ is H, then each $R^5$ is D.

In some embodiments, the JAK1/2 inhibitor is a compound of Formula I selected from the following compounds 100-130 in the table below (wherein $R^6$, $R^7$, and $R^8$ are each H), or a pharmaceutically acceptable salt thereof. In some embodiments, the inhibitor of JAK1 and/or JAK2 is a compound of Formula I selected from the following compounds 200-231 in the table below (wherein $R^6$, $R^7$, and $R^8$ are each D), or a pharmaceutically acceptable salt thereof.

| Compound | $R^1$ | Each $R^2$ | Each $R^3$ | $R^4$ | Each $R^5$ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | H | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | D | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK1/2 inhibitor is baricitinib, wherein one or more hydrogen atoms are replaced by deuterium atoms, or a pharmaceutically acceptable salt thereof. In some embodiments, the inhibitor of JAK1 and/or JAK2 is any of the compounds in U.S. Pat. No. 9,540,367 (which is incorporated herein by reference in its entirety), or a pharmaceutically acceptable salt thereof.

II. JAK1 Selective Inhibitors

In some embodiments, the JAK1 pathway inhibitor is selective for JAK1 over JAK2, JAK3, and TYK2 (i.e., a JAK1 selective inhibitor). Patients with bronchiolitis obliterans syndrome may benefit from selective JAK1 inhibition. Selective inhibitors of JAK1 may be efficacious while avoiding unnecessary and potentially undesirable effects of inhibiting other JAK kinases. Specifically, sparing of JAK2 inhibition may reduce the risk of cytopenias in post-lung transplant BOS patients following treatment with a selective JAK1 inhibitor such as Compound 1.

For example, the compounds described herein, or a pharmaceutically acceptable salt thereof, preferentially inhibit JAK1 over one or more of JAK2, JAK3, and TYK2. In some embodiments, the compounds inhibit JAK1 preferentially over JAK2 (e.g., have a JAK2/JAK1 $IC_{50}$ ratio >1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring ICso at 1 mM ATP (e.g., see Example A).

In some embodiments, the JAK1 pathway inhibitor is a compound of Table 2, or a pharmaceutically acceptable salt thereof. The compounds in Table 2 are selective JAK1 inhibitors (i.e., JAK1 pathway inhibitors, which are selective over JAK2, JAK3, and TYK2). The $IC_{50}$ values obtained by the method of Example A at 1 mM ATP are shown in Table 2.

TABLE 2

| Comp. No. | Prep. | Name | Structure | JAK1 IC$_{50}$ (nM) | JAK2/ JAK1 |
|---|---|---|---|---|---|
| 1 | U.S. 2011/ 0224190 (Example 1) | {1-{1-{3-Fluoro-2-(trifluoromethyl) isonicotinoyl]piperidin-4-yl}-3-[4-(7H-pyrrolo [2,3-d]pyrimidin-4-yl)-1H-pyrazol-1-yl] azetidin-3-yl}acetonitrile | 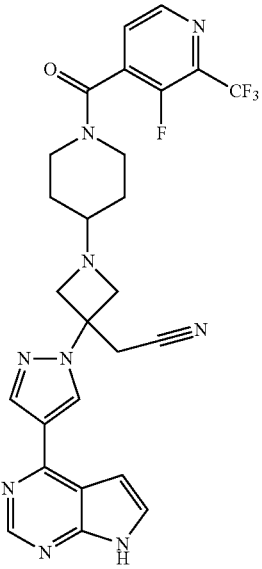 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 2 | U.S. 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl] piperidine-1-carboxamide | 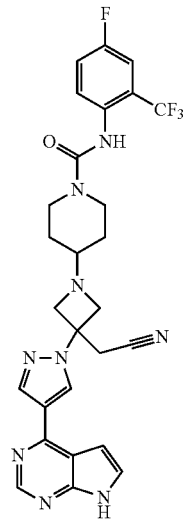 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 3 | U.S. 2011/ 0224190 (Example 85) | [3-[4-(7H-pyrrolo[2,3-d]pyrimidin-4-yl)-1H-pyrazol-1-yl]-1-(1-{[2-(trifluoromethyl) pyrimidin-4-yl]carbonyl}piperidin-4-yl)azetidin-3-yl]acetonitrile | 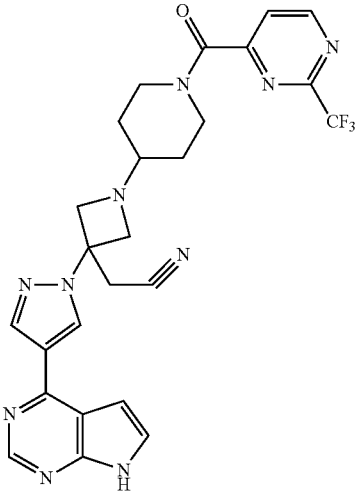 [SMILES: N#CCC1(n2cc(-c3ncnc4[nH]ccc34)cn2)CN(C2CCN(C(=O)c3ccnc(C(F)(F)F)n3)CC2)C1] | + | >10 |

TABLE 2-continued

| Comp. No. | Prep. | Name | Structure | JAK1 IC$_{50}$ (nM) | JAK2/ JAK1 |
|---|---|---|---|---|---|
| 4 | U.S. 2014/ 0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 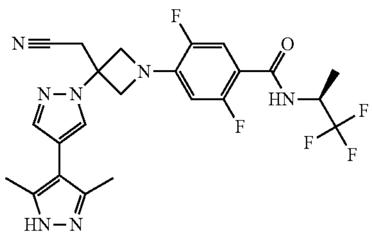 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 5 | U.S. 2014/ 0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 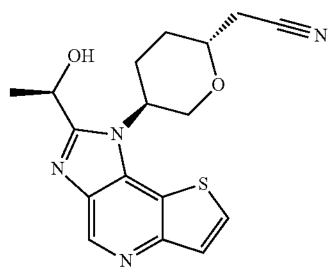 [SMILES: C[C@@H](O)c1nc2cnc3ccsc3c2n1[C@H]1CC[C@H](CC#N)OC1] | ++ | >10 |
| 6 | U.S. 2010/ 0298334 (Example 2)[a] | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 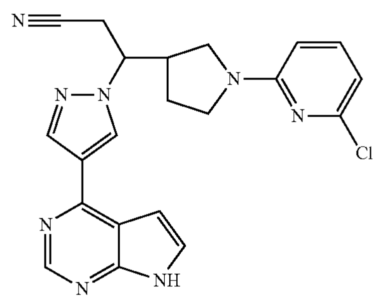 [SMILES: N#CCC(C1CCN(c2cccc(Cl)n2)C1)n1cc(-c2ncnc3[nH]ccc23)cn1] | + | >10 |
| 7 | U.S. 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 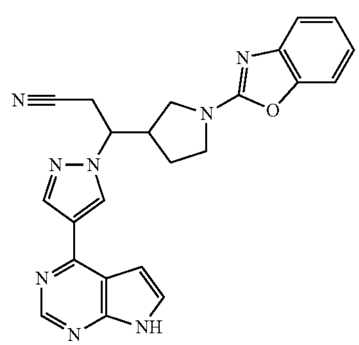 [SMILES: N#CCC(C1CCN(c2nc3ccccc3o2)C1)n1cc(-c2ncnc3[nH]ccc23)cn1] | + | >10 |
| 8 | U.S. 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 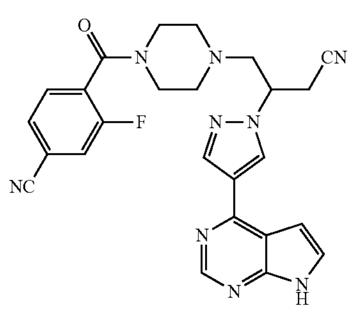 [SMILES: N#CCC(CN1CCN(C(=O)c2ccc(C#N)cc2F)CC1)n1cc(-c2ncnc3[nH]ccc23)cn1] | + | >10 |

TABLE 2-continued

| Comp. No. | Prep. | Name | Structure | JAK1 IC$_{50}$ (nM) | JAK2/ JAK1 |
|---|---|---|---|---|---|
| 9 | U.S. 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 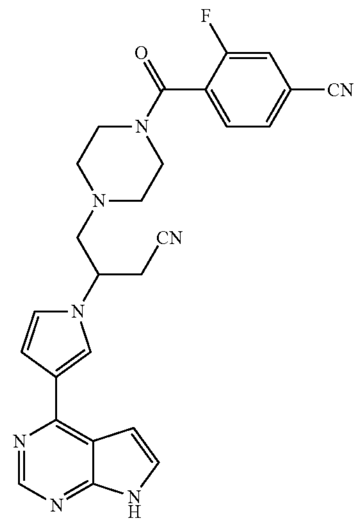 [SMILES: N#CCC(CN1CCN(C(=O)c2ccc(C#N)cc2F)CC1)n1ccc(-c2ncnc3[nH]ccc23)c1] | + | >10 |
| 10 | U.S. 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 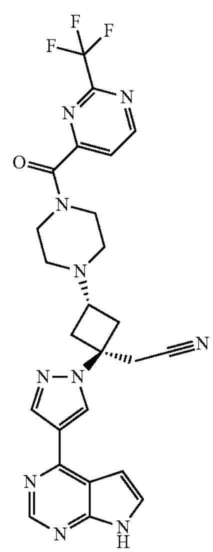 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |

TABLE 2-continued

| Comp. No. | Prep. | Name | Structure | JAK1 IC$_{50}$ (nM) | JAK2/ JAK1 |
|---|---|---|---|---|---|
| 11 | U.S. 2012/ 0149681 (Example 157) | {trans-3-(4-{[4-(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl] cyclobutyl}acetonitrile | 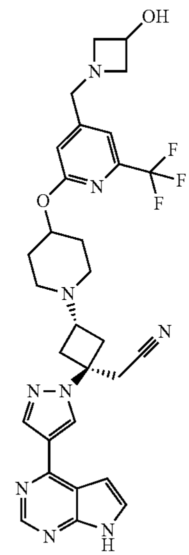 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |
| 12 | U.S. 2012/ 0149681 (Example 161) | {trans-3-(4-{[4-{[(2S)-2-(hydroxymethyl)pyrrolidin-l-yl]methyl}-6-(trifluoromethyl)pyridin-2-yl]oxy{piperidin-1-yl)-1-{4-(7H-pyrrolo[2,3-d{pyrimidin-4-yl)-1H-pyrazol-1-yl]cyclobutyl}acetonitrile | 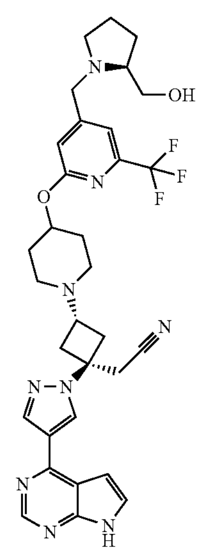 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |

TABLE 2-continued

| Comp. No. | Prep. | Name | Structure | JAK1 IC$_{50}$ (nM) | JAK2/ JAK1 |
|---|---|---|---|---|---|
| 13 | U.S. 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-{4-(7H-pyrrolo[2,3-d]pyrimidin-4-yl)-1H-pyrazol-1-yl]cyclobutyl}acetonitrile | 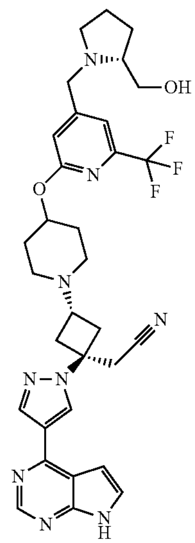 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | U.S. 2012/ 0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 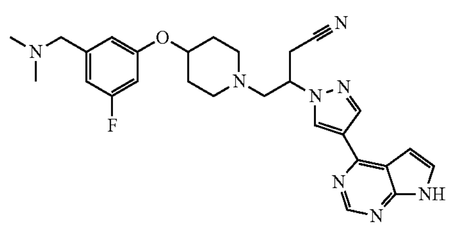 [SMILES: CN(C)Cc1cc(F)cc(OC2CCN(CC(CC#N)n3cc(-c4ncnc5[nH]ccc45)cn3)CC2)c1] | + | >10 |
| 15 | U.S. 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 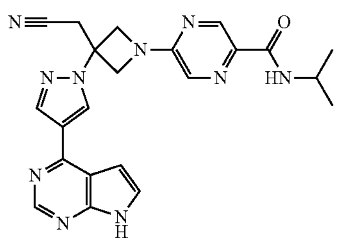 [SMILES: CC(C)NC(=O)c1cnc(N2CC(CC#N)(n3cc(-c4ncnc5[nH]ccc45)cn3)C2)cn1] | + | >10 |
| 16 | U.S. 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 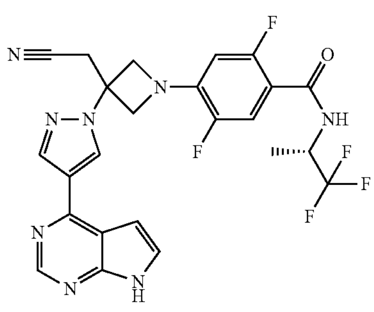 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | U.S. 2013/ 0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 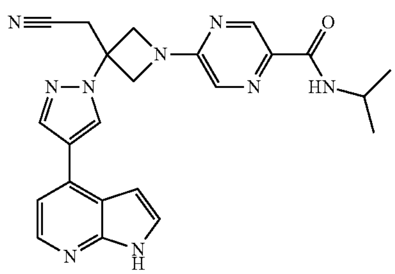 [SMILES: CC(C)NC(=O)c1cnc(N2CC(CC#N)(n3cc(-c4ccnc5[nH]ccc45)cn3)C2)cn1] | + | >10 |

TABLE 2-continued

| Comp. No. | Prep. | Name | Structure | JAK1 IC$_{50}$ (nM) | JAK2/JAK1 |
|---|---|---|---|---|---|
| 18 | U.S. 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 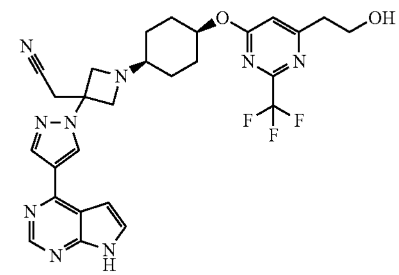 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | U.S. 2013/0045963 (Example 65) | {1-(cis-4-{[4-[(ethylamino)methyl]-6-(trifluoromethyl)pyridin-2-yl]oxy]cyclohexyl)-3-[4-(7H-pyrrolo[2,3-d]pyrimidin-4-yl)-1H-pyrazol-1-yl]azetidin-3-yl}acetonitrile | 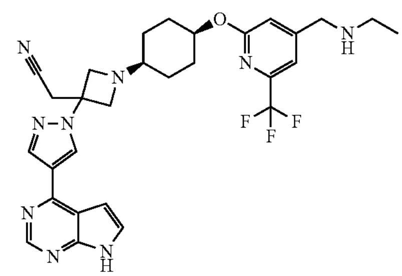 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | U.S. 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 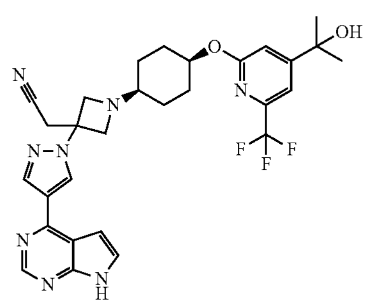 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | U.S. 2013/0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 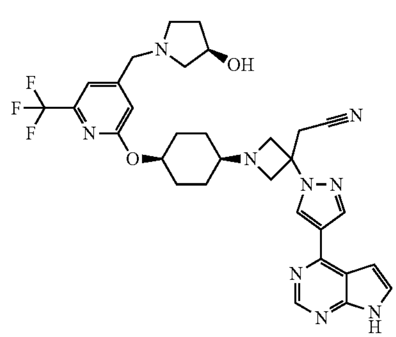 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | U.S. 2013/0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 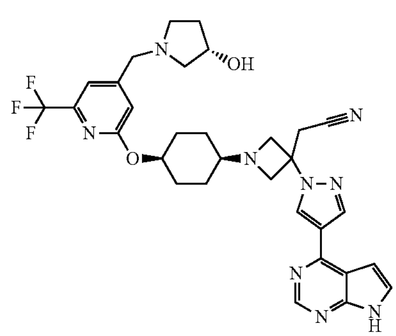 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |

TABLE 2-continued

| Comp. No. | Prep. | Name | Structure | JAK1 IC$_{50}$ (nM) | JAK2/ JAK1 |
|---|---|---|---|---|---|
| 23 | U.S. 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 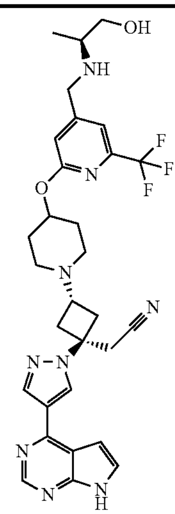 | + | >10 |
| 24 | U.S. 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 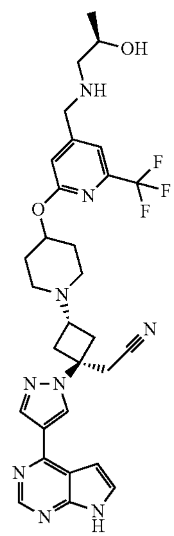 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | U.S. 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 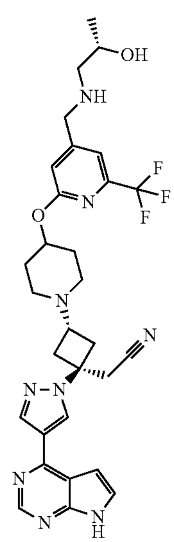 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 2-continued

| Comp. No. | Prep. | Name | Structure | JAK1 IC$_{50}$ (nM) | JAK2/ JAK1 |
|---|---|---|---|---|---|
| 26 | U.S. 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 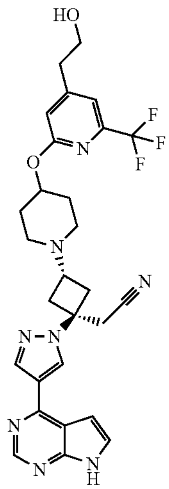 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example A for assay conditions)
++ means ≤100 nM (see Example A for assay conditions)
+++ means ≤300 nM (see Example A for assay conditions)
$^a$Data for enantiomer 1
$^b$Data for enantiomer 2

In some embodiments, the JAK1 pathway inhibitor is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK1 pathway inhibitor is {1-{1-[3-fluoro-2-(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. 2014/0343030, filed May 16, 2014, which is incorporated herein by reference in its entirety.

In some embodiments, the JAK1 pathway inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor is ((2R,5S)-5-{2-[(1R)-1-hydroxyethyl]-1H-imidazo[4,5-d]thieno[3,2-b]pyridin-2-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 2 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, JAK1 pathway inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 pathway inhibitor is a compound of Formula I

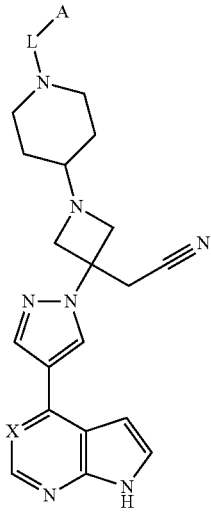

I or a pharmaceutically acceptable salt thereof, wherein:

X is N or CH;

L is C(=O) or C(=O)NH;

A is phenyl, pyridinyl, or pyrimidinyl each of which is optionally substituted with 1 or 2 independently selected $R^1$ groups; and each $R^1$ is, independently, fluoro, or trifluoromethyl.

In some embodiments, the compound of Formula I is {1-{1-[3-fluoro-2-(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula I is 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula I is [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile, or a pharmaceutically acceptable salt thereof.

In some embodiments, the JAK1 pathway inhibitor is a compound of Formula II

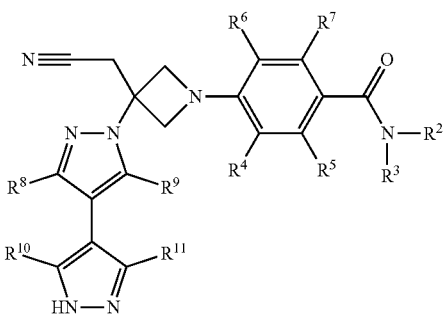

II or a pharmaceutically acceptable salt thereof, wherein:

$R^2$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^3$ is H or methyl;

$R^4$ is H, F, or Cl;

$R^5$ is H or F;

$R^6$ is H or F;

$R^7$ is H or F;

$R^8$ is H or methyl;

$R^9$ is H or methyl;

$R^{10}$ is H or methyl; and $R^{11}$ is H or methyl.

In some embodiments, the compound of Formula II is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is a compound of Formula III

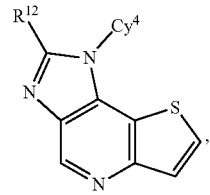

III or a pharmaceutically acceptable salt thereof, wherein:

$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and $R^{12}$ is —$CH_2$—OH, —CH($CH_3$)—OH, or —$CH_2$—$NHSO_2CH_3$.

In some embodiments, the compound of Formula III is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor is an isotopically-labeled compound, or a pharmaceutically acceptable salt thereof. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms, such as —$CD_3$ being substituted for —$CH_3$).

One or more constituent atoms of the compounds described herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, *Angew. Chem. Int. Ed.* 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al., *J. Label Compd. Radiopharm.* 2015, 58, 308-312). In particular, substitution at one or more metabolism sites may afford one or more of the therapeutic advantages.

Accordingly, in some embodiments, the JAK1 pathway inhibitor is a compound, wherein one or more hydrogen atoms in the compound are replaced by deuterium atoms, or a pharmaceutically acceptable salt thereof.

In some embodiments, the JAK1 pathway inhibitor, or a pharmaceutically acceptable salt thereof, is administered in a daily amount of from about 50 mg to about 600 mg on a free base basis. Accordingly, in some embodiments, the selective JAK1 pathway inhibitor, or a pharmaceutically acceptable salt thereof, is administered in a daily amount of about 50 mg, about 100 mg, about 150 mg, about 200 mg, about 250 mg, about 300 mg, about 350 mg, about 400 mg, about 450 mg, about 500 mg, about 550 mg, or about 600 mg on a free base basis.

In some embodiments, the JAK1 pathway inhibitor, or a pharmaceutically acceptable salt thereof, is administered at a daily amount of about 50 mg on a free base basis.

In some embodiments, the JAK1 pathway inhibitor, or a pharmaceutically acceptable salt thereof, is administered at a daily amount of about 100 mg on a free base basis.

In some embodiments, the JAK1 pathway inhibitor, or a pharmaceutically acceptable salt thereof, is administered at a daily amount of about 200 mg on a free base basis.

In some embodiments, the JAK1 pathway inhibitor, or a pharmaceutically acceptable salt thereof, is administered at a daily amount of about 300 mg on a free base basis.

In some embodiments, the JAK1 pathway inhibitor, or a pharmaceutically acceptable salt thereof, is administered at a daily amount of about 400 mg on a free base basis.

In some embodiments, the JAK1 pathway inhibitor, or a pharmaceutically acceptable salt thereof, is administered at a daily amount of about 500 mg on a free base basis.

In some embodiments, the JAK1 pathway inhibitor, or a pharmaceutically acceptable salt thereof, is administered at a daily amount of about 600 mg on a free base basis.

In some embodiments, the JAK1 pathway inhibitor, or a pharmaceutically acceptable salt thereof, is administered once daily at an amount of about 50 mg on a free base basis.

In some embodiments, the JAK1 pathway inhibitor, or a pharmaceutically acceptable salt thereof, is administered once daily at an amount of about 100 mg on a free base basis.

In some embodiments, the JAK1 pathway inhibitor, or a pharmaceutically acceptable salt thereof, is administered once daily at an amount of about 200 mg on a free base basis.

In some embodiments, the JAK1 pathway inhibitor, or a pharmaceutically acceptable salt thereof, is administered once daily at an amount of about 300 mg on a free base basis.

In some embodiments, the JAK1 pathway inhibitor, or a pharmaceutically acceptable salt thereof, is administered once daily at an amount of about 400 mg on a free base basis.

In some embodiments, the JAK1 pathway inhibitor, or a pharmaceutically acceptable salt thereof, is administered once daily at an amount of about 500 mg on a free base basis.

In some embodiments, the JAK1 pathway inhibitor, or a pharmaceutically acceptable salt thereof, is administered once daily at an amount of about 600 mg on a free base basis.

In some embodiments, the JAK1 pathway inhibitor, or a pharmaceutically acceptable salt thereof, is administered as one or more sustained release dosage forms each comprising the JAK1 pathway inhibitor, or a pharmaceutically acceptable salt thereof.

Provided herein is a method for treating bronchiolitis obliterans syndrome in a subject in need thereof in a subject, comprising administering to the subject a daily dose of from about 50 mg to about 600 mg on a free base basis of a JAK1 pathway inhibitor, or a pharmaceutically acceptable salt thereof, wherein the JAK1 pathway inhibitor, or a pharmaceutically acceptable salt thereof, is administered as one or more sustained release dosage forms comprising the JAK1 pathway inhibitor, or a pharmaceutically acceptable salt thereof.

Provided herein is a method for treating bronchiolitis obliterans syndrome in a subject in need thereof in a subject, comprising administering to the subject a daily dose of from about 100 mg to about 600 mg on a free base basis of a JAK1 pathway inhibitor, or a pharmaceutically acceptable salt thereof, wherein the JAK1 pathway inhibitor, or a pharmaceutically acceptable salt thereof, is administered as one or more sustained release dosage forms comprising the JAK1 pathway inhibitor, or a pharmaceutically acceptable salt thereof.

In some embodiments, the JAK1 pathway inhibitor, or pharmaceutically acceptable salt thereof, is administered as one or more sustained release dosage forms each comprising the JAK1 pathway inhibitor, or pharmaceutically acceptable salt thereof.

Sustained-release dosage forms of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof (Table 2, Compound 1) can be found in US Publ. No. 2015-0065484, filed Aug. 6, 2014, which is hereby incorporated by reference in its entirety. See also Example B infra.

Provided herein is a method for treating bronchiolitis obliterans syndrome in a subject in need thereof in a subject, comprising administering to the subject a once daily dose of from about 100 mg to about 600 mg on a free base basis of {1-{1-[3-fluoro-2-(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile, or a pharmaceutically acceptable salt thereof, wherein the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3- yl}acetonitrile, or a pharmaceutically acceptable salt thereof, is administered as one or more sustained release dosage forms.

The embodiments described herein are intended to be combined in any suitable combination as if the embodiments are multiply dependent claims (e.g., the embodiments related to the selective JAK1 pathway inhibitor and doses of the same, the embodiments related to any salt forms of the compounds disclosed herein, and the embodiments related to composition and/or administration can be combined in any combination). All possible combinations are not separately listed herein merely for the sake of brevity.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2, 4-triazole, 1H- and 2H-isoindole, and 1H- and 2H-pyrazole. Tautomeric forms can be in equilibrium or sterically locked into one form by appropriate substitution.

Compounds described herein can also include isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formulae (I), (II), or (III) or a compound of Table 2 can be optionally substituted with deuterium atoms, such as —$CD_3$ being substituted for —$CH_3$).

The term, "compound," as used herein is meant to include all stereoisomers, geometric isomers, tautomers, and isotopes of the structures depicted, unless the name indicates a specific stereoisomer. Compounds herein identified by name or structure as one particular tautomeric form are intended to include other tautomeric forms unless otherwise specified.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein.

Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The terms "individual," "patient," and "subject" are used interchangeably, and refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing bronchiolitis obliterans syndrome in an individual who may be predisposed to bronchiolitis obliterans syndrome (e.g., after a single or double lung transplant) but does not yet experience or display the pathology or symptomatology of the disease.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

Combination Therapies

The methods described herein can further comprise administering one or more additional therapeutic agents. These therapeutic agents include anti-inflammatory agents, steroids, immunosuppressants, or therapeutic anti-bodies.

Patients with a diagnosis of new onset post-lung transplant BOS are evaluated to ensure they are receiving optimal immunosuppression including compliance with prescribed medications and immunosuppressants used. For those patients on cyclosporine, there is evidence indicating that switching from cyclosporine to tacrolimus leads to a decrease in the loss of predicted FEV$_1$ (Sarahrudhi, K. et al. JTCS, April 2004, Vol. 127, No. 4). Once the immunosuppression regimen is optimized, there are few therapeutic options with any demonstrated efficacy. Options include:

Azithromycin: Azithromycin has demonstrated improvement in lung function, as defined by a >10 increase in FEV1, in approximately 35 to 40% of patients across multiple studies. This response appears to correlate with the presence of neutrophilia in BAL fluid (Vos, R. et al. *HLT*, 2010, Vol. 29, No. 12). Patients with an FEV$_1$ response to azithromycin had an overall survival advantage with azithromycin as compared to those who did not. In addition, a randomized study of prophylactic azithromycin compared to placebo in post-lung transplant BOS led to fewer cases of BOS, however, overall survival was not affected (Vos, R. et al. *Eur. Respir. J.* 2011, Vol. 37).

Extracorporeal Photopheresis (ECP): ECP has demonstrated modest activity in a number of single institution studies, the largest of which enrolled 51 patients. In this study, 61% of patients had prolonged stable disease defined by FEV$_1$ of −5 to +5 of pre-ECP baseline maintained over 6 months (Benden, E. C. et al. 2008 *Transplantation, Vol.* 86, No 11).

Montelukast: 30 patients were randomized to montelukast vs. placebo. Montelukast had no effect on lung function decline in the overall cohort. However, in a post-hoc subanalysis of BOS grade 1 patients, montelukast attenuated further decline of FEV$_1$ during the study period in both absolute and predicted FEV$_1$ (Ruttens, D. et al. Montelukast for bronchiolitis obliterans syndrome after lung transplantation: A randomized controlled trial. PLOS One April 6th 2018).

Accordingly, in some embodiments, methods provided herein comprise administering the JAK1 pathway inhibitor, or a pharmaceutically acceptable salt thereof and cyclosporine, or a pharmaceutically acceptable salt thereof.

In some embodiments, the methods provided herein comprise administering the JAK1 pathway inhibitor, or a pharmaceutically acceptable salt thereof, and azithromycin, or a pharmaceutically acceptable salt thereof. In some embodiments, azithromycin is administered at a daily amount of about 500 mg for one or two days.

In some embodiments, the methods provided herein comprise administering the JAK1 pathway inhibitor, or a pharmaceutically acceptable salt thereof, and extracorporeal photopheresis.

In some embodiments, the methods provided herein comprise administering the JAK1 pathway inhibitor, or a pharmaceutically acceptable salt thereof, and montelukast, or a pharmaceutically acceptable salt thereof. In some embodiments, montelukast is administered at a daily amount of from about 4 mg to about 10 mg (e.g., a daily amount of about 4 mg, about 5 mg, or about 10 mg).

In some embodiments, the methods provided herein comprise administering the JAK1 pathway inhibitor, or a pharmaceutically acceptable salt thereof, and tacrolimus, or a pharmaceutically acceptable salt thereof. In some embodiments, the tacrolimus is administered at a daily amount of from about 0.075 mg/kg/day to about 0.2 mg/kg/day.

In some embodiments, the methods provided herein comprise administering the JAK1 pathway inhibitor, or a pharmaceutically acceptable salt thereof, and mycophenolate mofetil, or a pharmaceutically acceptable salt thereof. In some embodiments, mycophenolate mofetil, or a pharmaceutically acceptable salt thereof, is administered at a daily amount of from about 500 to 1500 mg, e.g., a daily amout of about 1440 mg.

In some embodiments, the methods provided herein comprise administering the JAK1 pathway inhibitor, or a pharmaceutically acceptable salt thereof, and alemtuzumab. In some embodiments, alemtuzumab is administered as a first course of treatment and a second course of treatment twelve months after the first treatment course, wherein the first course of treatment comprises administration of about 12 mg/day on five consecutive days and the second course of treatment comprises administration of about 12 mg/day on three consecutive days.

In some embodiments, the methods provided herein comprise administering the JAK1 pathway inhibitor, or a pharmaceutically acceptable salt thereof, and methotrexate, or a pharmaceutically acceptable salt thereof. In some embodiments, the methotrexate is administered at a weekly amount of from about 7.5 mgs to about 30 mg (e.g., about 7.5 mg, about 10 mg, about 12.5 mg, about 15 mg, about 17.5 mg, about 20 mg, about 22.5 mg, about 25 mg, about 27.5 mg, or about 30 mg).

In some embodiments, the methods provided herein comprise administering the JAK1 pathway inhibitor, or a pharmaceutically acceptable salt thereof, and a corticosteroid, or a pharmaceutically acceptable salt thereof.

In some embodiments, the methods provided herein comprise administering the JAK1 pathway inhibitor, or a pharmaceutically acceptable salt thereof, and everolimus, or a pharmaceutically acceptable salt thereof. In some embodiments, the everolimus is administered at a daily amount of from about 2.5 mg to about 20 mg (e.g., a daily amount of about 2.5 mg, about 5 mg, about 10 mg, about 15 mg, or about 20 mg).

When more than one pharmaceutical agent is administered to a subject, they can be administered simultaneously, sequentially, or in combination (e.g., for more than two agents).

Compositions

The compounds can be administered in the form of pharmaceutical compositions. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The pharmaceutical compositions can contain, as the active ingredient, the compounds, or a pharmaceutically acceptable salt thereof, in combination with one or more pharmaceutically acceptable carriers (excipients). In some embodiments, the composition is suitable for topical administration. In making the compositions, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; and sweetening agents and flavoring agents. The compositions of the invention can be formulated so as to provide quick, sustained or delayed release of the active ingredient after administration to the patient by employing procedures known in the art.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

Kits

The present application also includes pharmaceutical kits useful, which include one or more containers containing a pharmaceutical composition comprising a therapeutically effective amount of the compound, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example A

In Vitro JAK Kinase Assay

JAK1 pathway inhibitors that can be used for the treatment of cytokine-related diseases or disorders are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds are measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 μL 45 mM EDTA, 300 nM SA-APC, 6 nM Eu-Py20 in assay buffer (Perkin Elmer, Boston, MA). Binding to the Europium labeled antibody takes place for 40 minutes and HTRF signal was measured on a Fusion plate reader (Perkin Elmer, Boston, MA). The compounds in Table 2 were tested in this assay and shown to have the ICso values in Table 2.

Example B

Preparation of Sustained Release Formulations of Compound 1

Sustained release tablets comprising Compound 1 were prepared with the excipients being in the amounts shown in the tables below. Protocol A was used for the SR1 tablets, Protocol B was used for the SR2 tablets, Protocol C was used for the SR3 tablets and the 25 mg SR tablets, and Protocol D was used for the SR4 tablets. These procedures are disclosed in US Patent Publ. No. 2015/0065484, which is directed to sustained release dosage forms of Compound 1.

Protocol A:

Step 1. Individually screen the adipic acid salt of Compound 1, microcrystalline cellulose, hypromelloses (Methocel K100 LV and Methocel K4M), and lactose monohydrate.

Step 2. Transfer the screened material from Step 1 to a suitable blender and mix.

Step 3. Transfer the blend from Step 2 to a suitable granulator and mix.

Step 4. Add purified water while mixing.

Step 5. Transfer the granules from Step 4 into a suitable dryer and dry until LOD is less than 3%.

Step 6. Screen the granules from Step 5.

Step 7. Mix screened Magnesium Stearate with granules in Step 6 in a suitable blender.

Step 8. Compress the final blend in Step 7 on a suitable rotary tablet press.

Protocol B:

Step 1. Individually screen the adipic acid salt of the compound of Formula I, microcrystalline cellulose, hypromellose and pregelatinized starch.

Step 2. Transfer the screened material from Step 1 to a suitable blender and mix.

Step 3. Transfer the blend from Step 2 to a suitable granulator and mix.

Step 4. Add purified water while mixing.

Step 5. Transfer the granules from Step 4 into a suitable dryer and dry until LOD is less than 3%.

Step 6. Screen the granules from Step 5.

Step 7. Individually screened polyox, butylated hydroxytoluene and colloidal silicone dioxide.

Step 8. Transfer the granules from Step 6 and material from Step 7 into a suitable blender and mix.

Step 9. Add screened Magnesium Stearate to the material in Step 8 and continue blending.

Step 10. Compress the final blend in Step 9 on a suitable rotary tablet press.

Protocol C:

Step 1. Individually screen lactose monohydrate, the adipic acid salt of the compound of Formula I, microcrystalline cellulose and hypromelloses through a suitable screen.

Step 2. Transfer the screened material from Step 1 to a suitable blender and mix.

Step 3. Transfer the blend from Step 2 to a suitable granulator and mix.

Step 4. Add purified water while mixing.

Step 5. Screen wet granules through a suitable screen.

Step 6. Transfer the granules from Step 5 into a suitable dryer and dry until LOD is less than 3%.

Step 7. Mill the granules from Step 6.

Step 8. Mix screened magnesium stearate with granules in Step 7 in a suitable blender.

Step 9. Compress the final blend in Step 8 on a suitable rotary tablet press.

Protocol D:

Step 1. Individually screen pregelatinized starch, the adipic acid salt of the compound of Formula I, hypromellose, and a portion of required microcrystalline cellulose through a suitable screen.

Step 2. Transfer the screened material from Step 1 to a suitable blender and mix.

Step 3. Transfer the blend from Step 2 to a suitable granulator and mix.

Step 4. Add purified water while mixing.

Step 5. Screen wet granules through a suitable screen.

Step 6. Transfer the granules from Step 5 into a suitable dryer and dry until LOD is less than 3%.

Step 7. Mill the granules from Step 6.

Step 8. Screen the remaining portion of microcrystalline cellulose and half of the sodium bicarbonate.

Step 9. Transfer the milled granules from Step 7 and screened materials from Step 8 into a suitable blender and mix.

Step 10. Screen the remaining portion of sodium bicarbonate and mix with blend in Step 9.

Step 11. Screen magnesium stearate and mix with blend in Step 10.

Step 12. Compress the final blend in Step 11 on a suitable rotary tablet press.

SR1: Composition of 100 mg Sustained Release Tablets

| Component | Function | Weight (mg/tablet) | Composition (wt %) |
|---|---|---|---|
| Adipic acid salt of the Compound 1 [a] | Active | 126.42 [a] | 21.1 |
| Microcrystalline Cellulose | Filler | 60.0 | 10.0 |
| Hypromellose (Methocel K100LV) | Release Control | 60.0 | 10.0 |
| Hypromellose (Methocel K4M) | Release Control | 60.0 | 10.0 |
| Lactose Monohydrate | Filler | 290.58 | 48.4 |
| Magnesium Stearate [b] | Lubricant | 3.0 | 0.5 |
| Purified Water [c] | Granulating Liquid | q.s. | — |
| Total | | 600.0 | 100 |

[a] Conversion factor for adipate salt to free base is 0.7911
[b] Added after granulation
[c] Removed during processing SR2: Composition of 100 mg Sustained Release Tablets

| Component | Function | Weight (mg/tablet) | Composition (wt %) |
|---|---|---|---|
| Adipic acid salt of Compound 1 [a] | Active | 126.4 [a] | 21.1 |
| Microcrystalline Cellulose | Filler | 180.0 | 30.0 |
| Hypromellose (Methocel K100LV) | Binder | 6.0 | 1.0 |
| Polyethylene Oxide (Polyox WRS 1105) [b] | Release Control | 180.0 | 30.0 |
| Pregelatinized Starch | Filler | 101.6 | 16.9 |
| Colloidal Silicon Dioxide [b] | Glidant | 3.0 | 0.5 |
| Butylated Hydroxytoluene [b] | Antioxidant | 0.012 | 0.002 |
| Magnesium Stearate [b] | Lubricant | 3.0 | 0.5 |
| Purified Water [c] | Granulating Liquid | q.s. | — |
| Total | | 600.0 | 100.0 |

[a] Conversion factor for adipate salt to free base is 0.7911
[b] Added after granulation
[c] Removed during processing SR3 (100 mg): Composition of 100 mg Sustained Release Tablets

| Component | Function | Weight (mg/tablet) | Composition (wt %) |
|---|---|---|---|
| Adipic acid salt of Compound 1 [a] | Active | 126.4 [a] | 21.1 |
| Microcrystalline Cellulose | Filler | 108.0 | 18.0 |
| Hypromellose (Methocel K100LV) | Release Control | 42.0 | 7.0 |
| Hypromellose (Methocel K4M) | Release Control | 30.0 | 5.0 |

SR3 (100 mg): Composition of 100 mg Sustained Release Tablets

| Component | Function | Weight (mg/tablet) | Composition (wt %) |
|---|---|---|---|
| Lactose Monohydrate | Filler | 290.6 | 48.4 |
| Magnesium Stearate [b] | Lubricant | 3.0 | 0.5 |
| Purified Water [c] | Granulating Liquid | q.s. | — |
| Total | | 600.0 | 100.0 |

[a] Conversion factor for adipate salt to free base is 0.7911
[b] Added after granulation
[c] Removed during processing SR4: Composition of 100 mg Sustained Release Tablets

| Excipient | Function | Weight (mg/tablet) | Composition (wt %) |
|---|---|---|---|
| Adipic acid salt of Compound 1 [a] | Active | 126.4 [a] | 21.1 |
| Microcrystalline Cellulose [d] | Filler | 104.6 | 17.4 |
| Hypromellose (Methocel K100LV) | Release Control | 210.0 | 35.0 |
| Pregelatinized Starch | Filler | 60.0 | 10.0 |
| Sodium Bicarbonate [b] | Gastric Floating Aid | 96.0 | 16.0 |
| Magnesium Stearate [b] | Lubricant | 3.0 | 0.5 |
| Purified Water [c] | Granulation Liquid | q.s. | — |
| Total | | 600.0 | 100.0 |

[a] Conversion factor for adipate salt to free base is 0.7911
[b] Added after granulation
[c] Removed during processing
[d] Partial added before and partial added after granulation 25 mg SR: Composition of 25 mg Sustained Release Tablets

| Component | Function | Weight (mg/tablet) | Composition (wt %) |
|---|---|---|---|
| Adipic acid salt of the compound of Formula I [a] | Active | 31.6 [a] | 12.6 |
| Microcrystalline Cellulose | Filler | 105.0 | 42.0 |
| Hypromellose, (Methocel K100LV) | Release Control | 25.0 | 10.0 |
| Hypromellose, (Methocel K4M) | Release Control | 25.0 | 10.0 |
| Lactose Monohydrate | Filler | 62.15 | 24.9 |
| Magnesium Stearate [b] | Lubricant | 1.25 | 0.5 |
| Purified Water [c] | Granulating Liquid | q.s. | — |
| Total | | 250 | 100.0 |

[a] Conversion factor for adipate salt to free base is 0.7911
[b] Added after granulation
[c] Removed during processing Example 1

Study of Safety and Efficacy of Compound 1 in Participants with Post-Lung-Transplant Bronchiolitis Obliterans Syndrome (BOS)

This Phase 1/2 study will evaluate the safety and efficacy of Compound 1 in participants with post-lung-transplant BOS.

TABLE 3

| Key Study Design Elements | |
|---|---|
| Study Phase | Phase 1/2 |
| Clinical Indication | Post-lung transplant bronchiolitis obliterans syndrome (BOS) |
| Population | Males and females who are at least 18 years of age who have undergone double lung transplantation within 1 to 5 years prior to screening and have a diagnosis of Grade 1 or 2 BOS. |
| Number of Participants | Phase 1 - Approximately 30 participants, to be treated at 3 different dose levels (n = 10 each) Phase 2 - Up to approximately 43 participants |
| Study Design | Phase 1 - Randomized, open-label Phase 2 - Single-arm, open label |

Phase 1 is a dose selection run-in that will employ a partially randomized, open-label, parallel-cohort design to assess the safety, tolerability, PK and PD and to determine the recommended phase 2 dose (RP2D) of Compound 1 in participants with post-lung transplant BOS. A total of 30 participants with Grade 1 or 2 BOS will be assigned to receive one of three Compound 1 dose levels (n=10 each); see Table 5 for additional details regarding Compound 1 dose levels. Participants taking no concurrent azole agent or a low to moderate CYP3A4 inhibiting azole (e.g., posaconazole or isovuconazle) at treatment initiation will be randomized to Dose Level 1 or 2. Participants taking itraconazole or voriconazole at treatment initiation will receive Dose Level 3. Upon completion of Phase 1, an interim futility analysis will be performed to determine the ORR (overall response rate) for all participants treated for ≥12 weeks. The study will proceed to Phase 2 if ≥1 responses (defined as ≥10% increase in $FEV_1$ compared to baseline, confirmed by 2 consecutive spirometric assessments ≥1 week apart) are observed at the dose level selected as the RP2D. Performance of spirometric assessments are described in the art; see, e.g., Miller, M. R. et al. *Eur. Respir.* 1 2005; 26: 319-338.

Phase 2 will employ a single-arm, open label design to evaluate the efficacy and further characterize the safety of Compound 1 at the RP2D. Compound 1 treatment will continue until progression of BOS (defined as a ≥10% decrease from baseline in FEV1, confirmed by 2 consecutive spirometric assessments ≥3 weeks apart), unacceptable toxicity, or withdrawal of consent.

Information regarding study drug and administration is provided below in Table 4.

TABLE 4

| Study Treatment Information | |
|---|---|
| Study treatment name: | Compound 1 |
| Dosage formulation: | SR tablet |
| Unit dose strength(s) | 100 mg tablet (100 mg of Compound 1 on a free base basis) |
| Route of administration: | Oral |
| Administration instructions: | During Phase 1, participants will be assigned to 1 of 3 dose levels, as outlined in Table 5, below. Compound 1 administration will continue daily at the assigned dose until treatment discontinuation. Compound 1 may be taken without regard to food except on PK days. Missed doses can be taken within 6 hours after the scheduled time of |

TABLE 4-continued

Study Treatment Information administration; however, if this window is not met, the missed dose will be documented as not taken and the next scheduled dose will be given.

TABLE 5

Compound 1 Dose Levels
Compound 1 dose levels are presented in Table 5 below:

| Compound 1 Dose Level: | Starting Dose (QD) | One Dose Level Reduction (QD) | Concurrent azole |
|---|---|---|---|
| Dose Level 1 | 200 mg | 100 mg | No azole or posaconazole |
| Dose Level 2 | 400 mg | 200 mg | No azole or posaconazole |
| Dose Level 3 | 100 mg | 50 mg | voriconazole or itraconazole |

Participants may have dose reductions or modifications of during the course of treatment based on AEs (adverse events), clinical evaluation, changes to concomitant medications, and laboratory assessments.

Study Population

Inclusion Criteria for this Study Can Include:
Male or female, 18 years of age or older
Written informed consent and assent (when appropriate) according to institutional standards and to comply with all study visits and procedures
Double lung transplantation within 1 to 5 years prior to screening
Documented post-transplant baseline $FEV_1$ (mean of the 2 highest values measured at least 3 weeks apart per ISHLT criteria) following functional recovery and stabilisation post-lung transplantation.
Confirmed BOS Grade 1 or 2 (per ISHLT 2002 criteria) diagnosed within 1 year of screening
Grade 1 BOS can be defined as a fractional decrease in $FEV_1$ to 66-80% of post-transplant baseline $FEV_1$.
Grade 2 BOS can be defined as a fractional decrease in $FEV_1$ to 51-65% of post-transplant baseline $FEV_1$.
Note: BOS grade can be determined by the average of 2 measurements made at least 3 weeks apart, without patient use of an inhaled bronchodilator.
Participants taking azithromycin may have initiated treatment at least 3 months prior to screening and should be on a stable dose (e.g., 250 mg/day at least 3 times per week).
Note: Participants should have stable or worsening $FEV_1$ after azithromycin administration, as assessed by 2 spirometric assessments at least 3 weeks apart prior to initiating treatment with Compound 1.
If participant is being treated with corticosteroids, the dose should be stable for 4 weeks prior to screening.
Willingness to avoid pregnancy or fathering children based on the specified criteria.

Exclusion Criteria for this Study Can Include:
History of a single lung transplant, heart-lung transplant, lung re-transplantation or any other solid organ transplant.
EBV negative participants (at the time of transplant) who received EBV Donor IgG positive lungs
Grade ≥3 BOS per ISHLT 2002 diagnostic criteria
$FEV_1$ decline attributable to cause(s) other than BOS, inflammatory complications of the lung allograft, antibody mediated rejection, infection, airway dysfunction, allograft compression, impaired graft inflation, vascular obstruction, transplant indication disease recurrence, organizing pneumonia, etc.
Has received any other systemic treatment for BOS (with the exception of azithromycin), including extracorporeal photophoresis, montelukast, and alemtuzumab.
Has had any change in immunosuppressive regimen in the 4 weeks prior to screening.
Untreated and/or symptomatic GERD.
Significant comorbidities including invasive fungal disease, B. Cepacia, Non-TB mycobacteria or TB
History of diffuse alveolar haemorrhage (DAH)
Current or prior treatment with a Janus kinase (JAK) inhibitor.
Participants with laboratory values at screening defined in Table 6.

TABLE 6

Exclusionary Laboratory Values

| | Laboratory Parameter | Exclusion Criterion |
|---|---|---|
| a | ANC | ≤1.5 × 10⁹/L |
| b | Platelet count | <150 × 10⁹/L |
| c | Hemoglobin | <9.0 g/dL |
| d | AST or ALT | ≥2 × ULN |
| e | Bilirubin | ≥1.5 × ULN, unless due to Gilbert's syndrome |
| f | Alkaline phosphatase | ≥3 × ULN |
| g | Creatinine clearance | <50 mL/min |
| h | Albumin | <3 mg/dL |
| i | INR | >1.5 |

Active HBV or HCV infection that requires treatment, or at risk for HBV reactivation (ie, positive HBsAg). Participants with negative HBsAg and positive total HBc antibody may be included if HBV DNA is undetectable at the time of screening. Participants who are positive for HCV antibody are eligible only if PCR is negative for HCV RNA. Participants whose immune status is unknown or uncertain can have results confirming immune status before enrollment. Prior serology results are acceptable for determining eligibility.
Known HIV infection.
History of active malignancy within 3 years of screening, excluding superficial basal and squamous cell carcinoma of the skin and adequately treated carcinoma in situ of the cervix.
Women who are pregnant or breastfeeding.
Anticipated need for live (including attenuated) vaccines during the first year of study.
Treatment with an investigational agent, procedure, or device within 30 days of randomization, or within 5 half-lives of the investigational product, whichever is longer.
Known allergies, hypersensitivity, or intolerance to any of the study medications, excipients, or similar compounds.
Inability or unlikeliness of the participant to comply with the dose schedule and study evaluations, in the opinion of the investigator.
Any condition that would, in the investigator's judgment, interfere with full participation in the study, including administration of study drug/treatment and attending required study visits; pose a significant risk to the participant; or interfere with interpretation of study data.

Inability of the participant (or legally authorized representative) to comprehend the ICF (informed consent form) or unwillingness to sign the ICF.

Various modifications of the invention, in addition to those described herein, will be apparent to those skilled in the art from the foregoing description. Such modifications are also intended to fall within the scope of the appended claims. Each reference cited in the present application, including all patent, patent applications, and publications, is incorporated herein by reference in its entirety.

What is claimed is:

1. A method of treating chronic lung allograft dysfunction in a subject, said method comprising administering to the subject 4 [3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

2. The method of claim 1, wherein the chronic lung allograft dysfunction is bronchiolitis obliterans syndrome.

3. The method of claim 1, wherein the subject is a lung transplant recipient.

4. The method of claim 1, wherein the subject is a double lung transplant recipient.

5. The method of claim 2, wherein the subject suffers from Grade Op, Grade 1, Grade 2, or Grade 3 bronchiolitis obliterans syndrome as determined by International Society for Heart and Lung Transplantation (ISHLT) criteria.

6. The method of claim 2, wherein the treating of bronchiolitis obliterans syndrome comprises about a 10% or greater increase in FEVs at twelve weeks following the first administration of the 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro- 1-methylethyl]benzamide, or a pharmaceutically acceptable salt thereof.

7. A method of reducing the risk of bronchiolitis obliterans syndrome in a subject, said method comprising administering to the subject 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

8. The method of claim 7, wherein the subject is a lung transplant recipient.

9. The method of claim 7, wherein the subject is a double lung transplant recipient.

10. A method of reducing the risk of lung re-transplantation in a subject, said method comprising administering to the subject 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

11. A method of reducing the risk of hospitalization in a subject, said method comprising administering to said subject an effective amount of 4-[3-(cyanomethyl)-3-(3',5'-dimethyl-1H,1'H-4,4'-bipyrazol-1-yl)azetidin-1-yl]-2,5-difluoro-N-R1S)-2,2,2-trifluoro-1-methylethyljbenzamide, or a pharmaceutically acceptable salt thereof, wherein said subject is (a) diagnosed with bronchiolitis obliterans syndrome; (b) has had a lung transplantation within 1 to 5 years prior to administering the, 4 [3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof, and (c) does not have a decrease in FEVs attributable to a cause other than bronchiolitis obliterans syndrome.

12. A method of treating bronchiolitis obliterans syndrome in a subject, said method comprising administering to the subject a pharmaceutically acceptable salt of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide.

13. The method of claim 1, wherein the pharmaceutically acceptable salt is 4-[3-(cyanomethyl)-3-(3',5'-dimethyl-1H,1'H-4,4'-bipyrazol-1-yl)azetidin-1-yl]-2,5-difluoro-N-[(15)-2,2,2-trifluoro-1-methylethyl]benzamide phosphoric acid salt.

14. The method of claim 7, wherein the pharmaceutically acceptable salt is 4-[3-(cyanomethyl)-3-(3',5'-dimethyl-1H,1'H-4,4'-bipyrazol-1-yl)azetidin-1-yl]-2,5-difluoro-N-[(15)-2,2,2-trifluoro-1-methylethyl]benzamide phosphoric acid salt.

15. The method of claim 10, wherein the pharmaceutically acceptable salt is 4-[3-(cyanomethyl)-3-(3',5'-dimethyl-1H,1'H-4,4'-bipyrazol-1-yl)azetidin-1-yl]-2,5-difluoro-N-[(15)-2,2,2-trifluoro-1-methylethyl]benzamide phosphoric acid salt.

16. The method of claim 11, wherein the pharmaceutically acceptable salt is 4-[3-(cyanomethyl)-3-(3',5'-dimethyl-1H,1'H-4,4'-bipyrazol-1-yl)azetidin-1-yl]-2,5-difluoro-N-[(15)-2,2,2-trifluoro-1-methylethyl]benzamide phosphoric acid salt.

17. The method of claim 12, wherein the pharmaceutically acceptable salt is 4-[3-(cyanomethyl)-3-(3',5'-dimethyl-1H,1'H-4,4'-bipyrazol-1-yl)azetidin-1-yl]-2,5-difluoro-N-[(15)-2,2,2-trifluoro-1-methylethyl]benzamide phosphoric acid salt.

* * * * *

UNITED STATES PATENT AND TRADEMARK OFFICE
CERTIFICATE OF CORRECTION

PATENT NO. : 11,896,595 B2
APPLICATION NO. : 17/854443
DATED : February 13, 2024
INVENTOR(S) : Richard L. Schaub and Kevin O'Hayer It is certified that error appears in the above-identified patent and that said Letters Patent is hereby corrected as shown below:

In the Claims

Column 43, Line 17, Claim 1, delete "4 [3-" and insert -- 4-[3- --;

Column 43, Line 33, Claim 6, delete "FEVS" and insert -- $FEV_1$ --;

Column 43, Line 36, Claim 6, delete "trifluoro- 1-" and insert -- trifluoro-1- --;

Column 44, Line 8, Claim 11, delete "N-R1S)" and insert -- N-[(1S) --;

Column 44, Line 8, Claim 11, delete "1-methylethyljbenzamide," and insert -- 1-methylethyl]benzamide, --;

Column 44, Line 12, Claim 11, delete "the, 4 [3-" and insert -- the 4-[3- --;

Column 44, Line 17, Claim 11, delete "FEVS" and insert -- $FEV_1$ --;

Column 44, Line 26, Claim 13, delete "(15)" and insert -- (1S) --;

Column 44, Line 31, Claim 14, delete "(15)" and insert -- (1S) --;

Column 44, Line 37, Claim 15, delete "(15)" and insert -- (1S) --;

Column 44, Line 41, Claim 16, delete "(15)" and insert -- (1S) --;

Column 44, Line 47, Claim 17, delete "(15)" and insert -- (1S) --.

Signed and Sealed this
Second Day of April, 2024

Katherine Kelly Vidal
*Director of the United States Patent and Trademark Office*